US011808724B2

United States Patent
Kinlen

(10) Patent No.: US 11,808,724 B2
(45) Date of Patent: Nov. 7, 2023

(54) CONDUCTIVE SENSOR SYSTEMS AND METHODS OF USE THEREOF

(71) Applicant: THE BOEING COMPANY, Chicago, IL (US)

(72) Inventor: Patrick J. Kinlen, Fenton, MO (US)

(73) Assignee: The Boeing Company, Arlington, VA (US)

( * ) Notice: Subject to any disclaimer, the term of this patent is extended or adjusted under 35 U.S.C. 154(b) by 148 days.

(21) Appl. No.: 17/237,603

(22) Filed: Apr. 22, 2021

(65) Prior Publication Data

US 2021/0404984 A1 Dec. 30, 2021

Related U.S. Application Data

(60) Provisional application No. 63/044,102, filed on Jun. 25, 2020.

(51) Int. Cl.
*G01N 17/02* (2006.01)
*G01N 33/208* (2019.01)
(Continued)

(52) U.S. Cl.
CPC ........... *G01N 27/20* (2013.01); *G01N 27/041* (2013.01); *G01N 17/02* (2013.01); *G01N 27/02* (2013.01);
(Continued)

(58) Field of Classification Search
CPC ...... G01N 17/02; G01N 27/42; G01N 33/208; G01N 2033/0096
See application file for complete search history.

(56) References Cited

U.S. PATENT DOCUMENTS 2,849,521 A * 8/1958 Heise ................. H01M 50/184
429/185
5,505,836 A * 4/1996 Miyahara ........... G01N 27/3335
204/418

(Continued)

OTHER PUBLICATIONS

J. Shen, A double-mode cell to measure pitting and crevice corrosion, Materials and Corrosion, 2019(70), p. 2228-37. (Year: 2019).*

(Continued)

*Primary Examiner* — Caitlyn Mingyun Sun
(74) *Attorney, Agent, or Firm* — Patterson + Sheridan, LLP

(57) ABSTRACT

The present disclosure provides a sensor system including one or more sensors having a first container fluidly coupled to a second container, the second container being configured to receive a conductive media from the first container. A first movable element is slidingly engaged with the first container to cause the second container to receive the conductive media from the first container. A first electrode is positioned in the first cavity and electrically coupled to the conductive media. In some examples, a second electrode is electrically coupled to the first electrode and the conductive media. The sensor deposits the conductive media on a working electrode to form an electrochemical cell and obtain one or more material properties of the working electrode. In some examples, the sensor system includes an array of sensors which deposit the conducive media in multiple locations on a working electrode to generate a material property map.

16 Claims, 10 Drawing Sheets

(51) Int. Cl.
  *G01N 33/00*  (2006.01)
  *G01N 27/20*  (2006.01)
  *G01N 27/04*  (2006.01)
  *G01N 27/02*  (2006.01)
  *G01N 27/42*  (2006.01)

(52) U.S. Cl.
  CPC ........... *G01N 27/42* (2013.01); *G01N 33/208* (2019.01); *G01N 2033/0096* (2013.01)

(56) References Cited

U.S. PATENT DOCUMENTS

| | | | | |
|---|---|---|---|---|
| 2014/0354307 | A1* | 12/2014 | Clarke | G01N 17/04 324/700 |
| 2015/0247818 | A1* | 9/2015 | Silvester | G01N 27/49 429/492 |
| 2018/0275081 | A1* | 9/2018 | Brady | G01N 27/025 |
| 2019/0156598 | A1* | 5/2019 | Palmer, Jr. | G01N 17/006 |

OTHER PUBLICATIONS

KR 2020-0062956 machine translation. (Year: 2020).*
H. Yu, et al., Threshold chloride level and characteristics of reinforcement corrosion initiation in simulated concrete pore solutions, Construction and Building Materials, 2012(26), p. 723-29. (Year: 2012).*
JPH0743335B2 machine translation. (Year: 1995).*
SigmaAldrich—Peo Peg (Year: 2022).*
Blanca Ramíez Barat, Emilio Cano, Paola Letardi, "Advances in the design of a gel-cell electrochemical sensor for corrosion measurements on metallic cultural heritage," Sensors and Actuators B: Chemical, pp. 1-9, Year: 2018.
K. Charoenkitamorn, C. Chotsuwan, S. Chaiyo, W. Siangproh, O. Chailapakul, "A new ready-to-use gel-based electrolyte for paraquat sensor," Sensors and Actuators B: Chemical, pp. 1-10, Year: 2020.
A.M. Panindre, K.H. Chang, T. Weirich, and G.S. Franel, "Technical Note: Syringe Cell for Electrochemical Testing," Corrosion Science Section, dated: May 18, 2018, pp. 847-890.

* cited by examiner

US 11,808,724 B2

CONDUCTIVE SENSOR SYSTEMS AND METHODS OF USE THEREOF

CROSS-REFERENCE TO RELATED APPLICATIONS

This application claims benefit of U.S. provisional patent application Ser. No. 63/044,102, filed Jun. 25, 2020, which is herein incorporated by reference in its entirety.

FIELD

Aspects of the present disclosure relate to the non-destructive inspection and testing of surfaces, including coated surfaces and three-dimensional structures.

BACKGROUND

Various components can include coatings, three-dimensional structures, and coatings formed on and/or in three-dimensional structures. These components can be included in automobiles, aircraft, or other vehicles and can experience wide ranges of pressures, temperatures, or chemically corrosive environments. These environments can cause degradation of the components, including degradation of the coatings or the three-dimensional structures. In some situations, foreign materials may be deposited or formed on the coatings or three-dimensional structures during component use that could be harmful to the component. Detection of degradation or foreign material formation and identification can involve destructive testing methods, especially in the case of determining corrosion in three-dimensional structures. Accordingly, there is a need for systems and methods of testing the uniformity and integrity of coatings and three-dimensional structures, as well as characterizing foreign materials deposited or otherwise formed on or inside of components having coatings or three-dimensional structures.

SUMMARY

The present disclosure provides a sensor system, in one aspect, the sensor system including: a sensor having a sensor body, the sensor body having a first container and a second container. The first container having a first inside surface defining a first cavity, and the second container having a second inside surface defining a second cavity. The first container is fluidly coupled to the second container. Further, in aspects of the sensor system, and a first electrode positioned in the first cavity, the first electrode being electrically coupled to the conductive media. Furthermore, in the sensor system, a first movable element is positioned in the first cavity, the first movable element being slidingly engaged with the first inside surface of the first container and configured to cause the second container to receive the conductive media from the first container.

In one aspect, in combination with any example sensor system above or below, the sensor system further includes a first electrode formed from silver and having a silver chloride coating formed thereon.

In one aspect, in combination with any example sensor system above or below, the sensor system further includes a conductive media is disposed in the first cavity, a second electrode electrically coupled to the first electrode and electrically coupled to the conductive media, the second electrode being formed from platinum, the second cavity being configured to receive the conductive media from the first cavity.

In one aspect, in combination with any example sensor system above or below, the sensor system further includes a second electrode configured as a linear element or as a closed loop.

In one aspect, in combination with any example sensor system above or below, the sensor system further includes a first inside diameter of the first container that is greater than a second inside diameter of the second container.

In one aspect, in combination with any example sensor system above or below, the sensor system further includes a plurality of sensors, each sensor of the plurality of sensors being connected to at least one adjacent sensor via a connection mechanism along a shared plane.

In one aspect, in combination with any example sensor system above or below, the sensor system further includes a plurality of sensors, a plurality of connection mechanisms, and a sensor support having an outside surface, an inside surface, and a central axis. Each sensor of the plurality of sensors is removably coupled to the sensor support via at least one connection mechanism of the plurality of connection mechanisms.

In one aspect, in combination with any example sensor system above or below, the sensor system further includes a sensor support having a plurality of portions, each portion of the plurality of portions being removably coupled to an adjacent portion, and each portion is independently adjustable relative to the central axis.

The present disclosure provides another sensor system, in one aspect, the sensor system including: a sensor having a sensor body having a first container and a second container. The first container includes a first inside surface, the first inside surface defining a first cavity, and the second container includes a second inside surface defining a second cavity, the second container being fluidly coupled to the first container. The sensor system further includes a conductive media disposed in the first cavity, the second cavity being configured to receive the conductive media from the first cavity. In some aspects, the sensor system further includes a first electrode disposed in the first cavity and electrically coupled to the conductive media, the first electrode including a metallic wire having a metallic salt coating, and a second electrode, the second electrode being electrically coupled to the first electrode and to the conductive media. The sensor system further includes a first movable element positioned in the first cavity, the first movable element being slidingly engaged with the first inside surface of the first container and configured to cause the second container to receive the conductive media from the first container.

In one aspect, in combination with any example sensor system above or below, the sensor system further includes a power supply configured to apply a current to the sensor system.

In one aspect, in combination with any example sensor system above or below, the sensor system further includes that the conductive media has a viscosity from about 50,000 centipoise (cps) to about 1 million cps.

In one aspect, in combination with any example sensor system above or below, the sensor system further includes that the conductive media has a water content from about 5 wt. % to about 65 wt. %.

In one aspect, in combination with any example sensor system above or below, the sensor system further includes a conductive media having a first element and a second element, and the first element is a conductive element that forms a colloidal suspension with the second element.

In one aspect, in combination with any example sensor system above or below, the sensor system further includes a first element selected from the group consisting of: a salt, a plurality of polymer nanoparticles, a plurality of metallic nanoparticles, and combinations thereof.

In one aspect, in combination with any example sensor system above or below, the sensor system further includes a second element selected from the group consisting of: aloe, polyethylene glycol (PEG), polyacrylamide, and combinations thereof.

In one aspect, in combination with any example sensor system above or below, the sensor system further includes a ratio of a volume percentage (vol. %) of the first element to the second element is from about 1:100 to about 1:1.

In one aspect, in combination with any example sensor system above or below, the sensor system further includes a plurality of executable logic stored on a non-transitory computer-readable medium communicatively coupled to the sensor system, the plurality of executable logic being configured to execute a measurement program to determine a material property of a working electrode, the working electrode having a portion of the conductive media disposed thereon and being electrically coupled to the sensor body via the portion of the conductive media.

The present disclosure provides a method of testing, in one aspect, the method of testing including: positioning a sensor system relative to a working electrode; depositing, via a sensor system, a conductive media on the working electrode. The conductive media is electrically coupled to at least one electrode of the sensor system, and depositing the conductive media electrically couples the working electrode to the sensor system. The method further includes performing a test on the working electrode. Performing the test includes: generating, via a power supply, a current through the sensor system and the working electrode; and receiving, in response to the generating of the current, at least one output, and the at least one output indicates an electrochemical property of the working electrode.

In one aspect, in combination with any example method of testing above or below, the method further includes: forming a map of a portion of the working electrode, the sensor system having a plurality of sensors, the forming of the map including: prior to applying the current, positioning the plurality of sensors in a plurality of locations along at least one surface of the working electrode; and depositing the conductive media on the plurality of locations to electrically couple each sensor of the plurality of sensors to the working electrode.

In one aspect, in combination with any example method of testing above or below, the method further includes that the working electrode is formed as a three-dimensional component including a plurality of surfaces such that at least one sensor of the sensor system is positioned inside of the working electrode, and the depositing of the conductive media causes the conductive media to contact two or more surfaces of the plurality of surfaces.

BRIEF DESCRIPTION OF THE DRAWINGS

So that the manner in which the above recited features can be understood in detail, a more particular description, briefly summarized above, may be had by reference to example aspects, some of which are illustrated in the appended drawings.

DETAILED DESCRIPTION

Figure 1A:
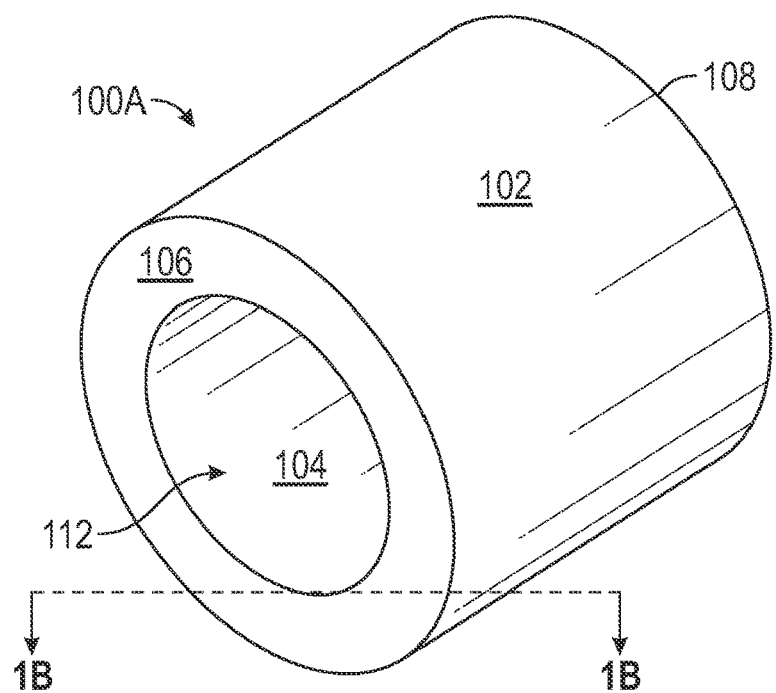
FIG. 1A depicts a component that can be inspected according to one or more aspects of the sensor systems of the present disclosure.

The present disclosure relates to using an electrochemical sensor system to evaluate component integrity and suitability for use. The sensor systems discussed herein are configured to perform non-destructive tests to determine a variety of material properties to determine if and when maintenance and remediation activities are to be performed. The components discussed herein can include aircraft, aerospace, automotive, rail, marine, or other components having one or more of a coating (single or multi-layered) or a three-dimensional structure. The coatings discussed herein that can be evaluated by the sensor systems can include polymers, elastomers, metals, ceramics, and can be reinforced with particles of varying types and sizes.

The sensor systems and methods discussed herein can be used to characterize materials by determining, for example, (1) a uniformity of a coating, (2) a composition of a coating, (3) an integrity of a coating (e.g., is the coated component suitable for use), (4) a composition of a material formed or deposited on a component, and/or (5) an integrity of a two or three-dimensional structure. These evaluations can be used to determine a degree of corrosion on a surface or underneath a coated surface. The data collected can be used to determine if repairs are needed or if the component evaluated can be used/kept in use without maintenance. The sensor systems discussed herein can be configured as a hand-held device, such that an operator can use the sensor system in a hangar or on an aircraft carrier to determine a condition of an aircraft component. While aircraft components are used as an example of components that can be tested using the sensor systems discussed herein, the present disclosure is not limited to such applications and other systems or components of systems can also be evaluated using the sensor systems discussed herein. In some aspects of the sensor systems discussed herein, the sensor systems can include arrays of varying sizes and geometries that can be used to generate maps of coatings and component structures.

In one example, the sensor systems discussed herein can include a single sensor coupled to a power supply to form an electrochemical cell. The sensors discussed herein can include a reference electrode, an auxiliary electrode, or both electrodes. As discussed herein, a "reference electrode" can be an electrode having an accurately maintained (known) potential, which other potentials can be measured against. Further, as discussed herein, an "auxiliary electrode" is a counter electrode which the current of the electrochemical cells of the sensor systems discussed herein flow through. The electrochemical cells discussed herein are formed using at least one electrode discussed above, a conductive media, and a working electrode. As discussed herein, a "working electrode" includes any surface or plurality of surfaces from which a material property is to be measured where the electrochemical cell reaction occurs.

The material properties determined using the sensor systems discussed herein can include a composition, an electrical property, a chemical property, an electro-chemical property, or a physical property such as a material thickness or uniformity of thickness. The working electrodes discussed herein can include smooth surfaces, surfaces including three-dimensional nano-structures, or three-dimensional structures such that the working electrode can encompass one or more surfaces. The working electrodes can include coated or uncoated structures formed from polymers, elastomers, ceramics, metals, or combinations thereof. The working electrodes such as the three-dimensional structures discussed herein can be formed from aluminum, nickel, steel, chromium, alloys or superalloys or combinations thereof. The sensor systems can use various types of electrochemical tests to determine these material properties, including the difference in potential across the working electrode interface, a reaction rate based on a current density, or a surface impedance.

In some aspects of the present disclosure, the sensor systems discussed herein can include a single sensor coupled to a power supply and coupled to smart technology, e.g., hardware and software including a non-transitory computer-readable medium storing a plurality of logic that is executable by a processor. A single sensor system may be used to identify foreign matter deposited or formed on a component. The smart technology can include wireless communication capability and can be used to, for example, (1) determine a quantity of conductive media to deposit, (2) determine a current to apply, (3) one or more electrochemical tests to perform, (4) receive data from the tests, (5) analyze the data received, and/or (6) determine and indicate an action to take based upon the data analysis. In some examples, when the sensor system includes a visual feedback mechanism, (6) can include a red, yellow, or green light on the sensor system, or a readout of data in list or map form. In other examples, the sensor systems discussed herein can be configured as arrays of two or more sensors in various geometric configurations that can be coupled to a power supply and, further coupled to smart technology. The arrays can be used to deposit conductive media on a plurality of locations on a working electrode in order to determine coating uniformity. The sensor systems discussed herein can be used to generate a map of material properties, either by using a single sensor to deposit conductive media in multiple locations in series of tests, or by using a sensor array to obtain information regarding a plurality of locations across a working electrode.

Example Components to be Evaluated by Sensor Systems

FIG. 1A depicts a component 100A that can be inspected using one or more aspects of the sensor systems discussed herein. The component 100A can be a nacelle having a first end 106 opposite a second end 108. The component 100A can further include an outside surface 102 and an inside surface 104 defining a cavity 112 extending from the first end 106 to the second end 108. In one example, the outside surface 102 includes a first coating (shown below as 114 in FIG. 1B) having one or more layers. In another example, which can be combined with other examples herein, the inside surface 104 can have a second coating (shown below as 116 in FIG. 1B) having one or more layers.

Figure 1B:
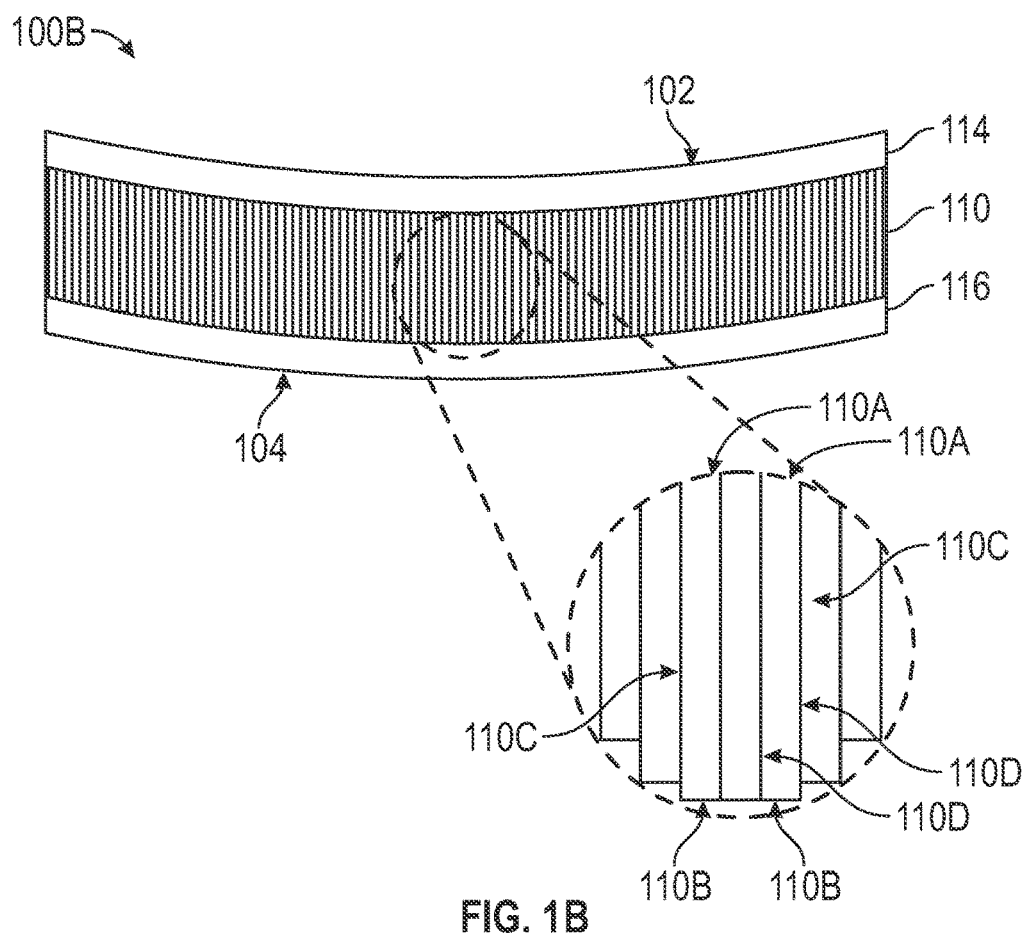
FIG. 1B depicts a portion 100B of a cross-section of the component 100A taken along line 1B-1B in FIG. 1A.

FIG. 1B depicts a portion 100B of a cross-section of the component 100A taken along line 1B-1B in FIG. 1A. The portion 100B includes the outside surface 102 that can include a first coating 114 having one or more layers, formed on top of a three-dimensional structure 110. Further in FIG. 1B, there is the inside surface 104, which can include a second coating 116 having one or more layers. A portion of the three-dimensional structure 110 is shown as an inset of FIG. 1B. As shown in the inset, the three-dimensional structure 110 includes a plurality of cells, each defined by an inside wall 110D and a bottom surface 110B forming a cavity 110C. The three-dimensional structure 110 further includes a top end 110A, illustrated as an open in the inset figure, where the first coating 114 of the outside surface 102 can be deposited. During assembly of the component 100A, one or more of the first coating 114 on the outside surface 102, the second coating 116 on the inside surface 104, or surfaces (110D, 110B) of the three-dimensional structure can be damaged and/or, with respect to the coatings, may not be uniform. Similarly, during use of the component 100A, one or more of the first coating 114 on the outside surface 102, the second coating 116 on the inside surface 104, or surfaces (e.g., 110D, 110B) of the three-dimensional structure can be damaged and/or have foreign matter formed or deposited thereon. While the outside surface 102 and the inside surface 104 are shown in FIG. 1B as having coatings (114, 116) formed thereon, in other examples, one or more of the outside surface 102 or the inside surface 104 may include a metallic, polymer, ceramic, or other material which does not have a coating formed thereon. The sensor systems discussed herein can be used to inspect coating uniformity, composition, as well as overall component integrity including the integrity of the plurality of cells of the three-dimensional structure 110, in contrast to a single surface of the plurality of cells, as well as the identification of foreign material formed on or in any aspect of the component 100A. Once aspects of the component 100A discussed above are inspected, remediation/maintenance actions can scheduled for an appropriate timeframe based upon the results of the testing.

Figure 1C:
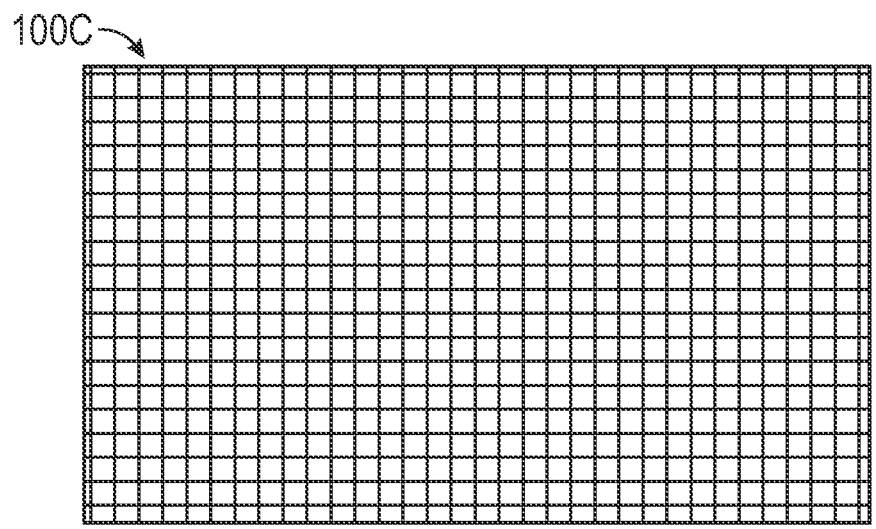
FIG. 1C depicts a first top structure including a plurality of polygons configured as squares that can be inspected according to one or more aspects of the sensor systems of the present disclosure.
Figure 1D:
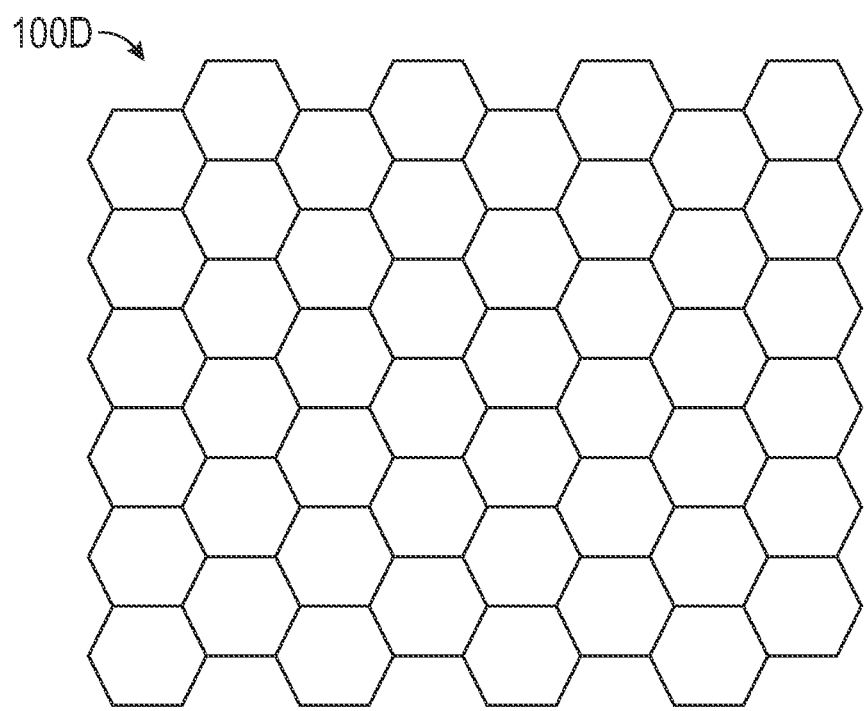
FIG. 1D depicts a second top structure having a plurality of polygons configured as hexagonal structures that can be inspected according to one or more aspects of the sensor systems of the present disclosure.

FIGS. 1C and 1D are top views of the top end 110A of the three-dimensional structure 110 from FIG. 1B. FIG. 1C depicts a first top structure 100C including a plurality of polygons configured as squares. FIG. 1D depicts a second top structure 100D having a plurality of polygons configured as hexagonal structures, which can be referred to herein as a "honeycomb" structure. In different examples of the component 100A, the plurality of cells of the three-dimensional structure 110 can have varying cross-sectional shapes.

Sensor Systems

Figure 2A:
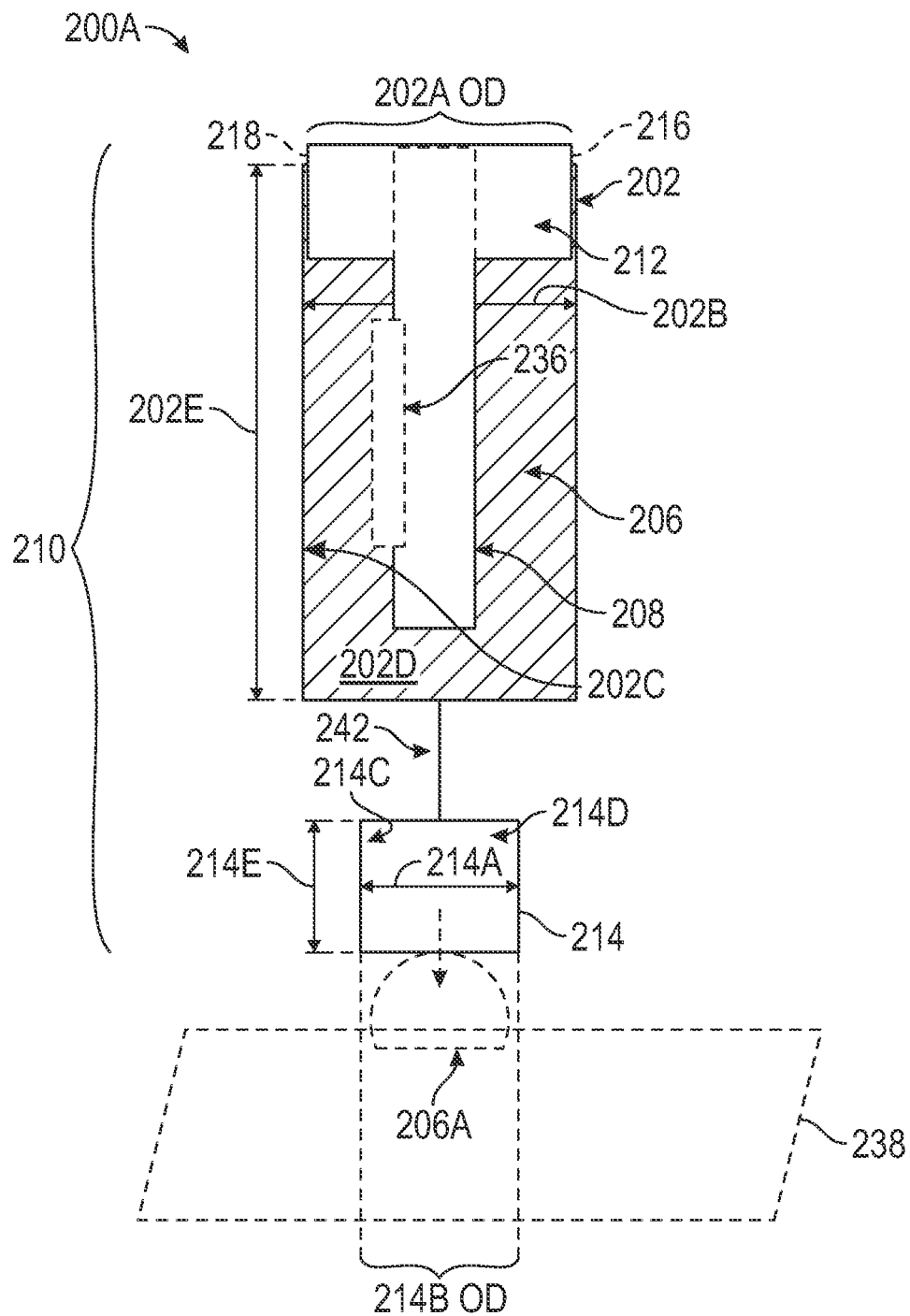
FIG. 2A depicts a sensor system according to aspects of the present disclosure.

FIG. 2A depicts a sensor system 200A according to aspects of the present disclosure. The sensor system 200A illustrates a sensor that includes a sensor body 210, the sensor body 210 includes a first container 202 that can be removably or permanently coupled to a second container 214. As used here, "removably coupled" is used to refer to the coupling of two or more elements, such as a two or more sensor systems, or individual elements of a sensor system (e.g., two or more containers), or a coupling between a sensor system and a structure to be evaluated by the sensor system, which can subsequently be un-coupled without damage to either coupled element. As used herein, "permanently coupled"" is used to refer to the coupling of two or more elements, such as a two or more sensor systems, or individual elements of a sensor system (e.g., two or more containers), which cannot be un-coupled without causing damage to one or both coupled elements or structures. In one example, the first container 202 is fluidly coupled to the second container 214. As used herein, "fluidly coupled" is used to refer to the coupling of two or more elements, such as a two or more sensor systems, or individual elements of a sensor system (e.g., two or more containers), or a coupling between a sensor system and a structure to be evaluated by the sensor system, which are configured as to transport fluid among and between the two or more elements or systems. In one example, the first container 202 can be formed from polymers, elastomers, or glass, or combinations thereof. In some examples, which can be combined with other examples herein, the first container 202 can be a reciprocating pump including a connector, such as a for example a syringe body. The first container 202 and the second container 214 can be coupled via a connection mechanism 242. The connection mechanism 242 can include a leur lock. Similarly, the second container 214 can be formed from one or more polymers, elastomers, or glass. The second container 214 can be formed as a tube or tubing. In one example, the second container 214 is formed from a flexible material such that it can be positioned inside of three-dimensional structures without breaking, and without causing damage to the three-dimensional structure. In one example, the first container 202 can be formed from the same material as the second container 214. In another example, which can be combined with other examples herein, the first container 202 can be formed from one or more different materials as compared to the second container.

In one example, the first container 202 has a first inside diameter 202B, a first outside diameter 202A, and a first inside surface 202C defining a first cavity 202D. The first container 202 can further be defined by a first length 202E. In another example, which can be combined with other examples herein, the second container 214 has a second inside diameter 214A, an outside diameter 214B, and a second inside surface 214C defining a second cavity 214D. The second container 214 can have a second length 214E. In one example, the first length 202E of the first container 202 can be greater than the second length 214E of the second container 214 by from about 10% to about 100%. In another example, the first length 202E of the first container 202 can be greater than the second length 214E of the second container 214 by from about 30% to about 75%. In yet another example, the first length 202E of the first container 202 can be greater than the second length 214E of the second container 214 by from about 45% to about 60%. The relative container lengths discussed herein can be configured as such for varying purposes, including when the working electrodes discussed herein have various geometries and configurations. For example, some relative container lengths can be desirable when depositing conductive media 206 on one or more surfaces of a working electrode. The relative container lengths discussed herein can further configured to retain varying amounts of conductive media in the first container 202.

In some examples, which can be combined with other examples herein, the first inside diameter 202B of the first container 202 is greater than the second inside diameter 214A of the second container 214. In one example, the first inside diameter 202B of the first container 202 is greater than the second inside diameter 214A of the second container 214 by from about 10% to about 100%. In another example, the first inside diameter 202B of the first container 202 is greater than the second inside diameter 214A of the second container 214 by from about 20% to about 70%. In still another example, the first inside diameter 202B of the first container 202 is greater than the second inside diameter 214A of the second container 214 by from about 35% to about 50%. The relative container diameters discussed herein can configured as such for varying purposes, including when the working electrodes discussed herein have various geometries and configurations. For example, some relative container lengths can be desirable when depositing conductive media 206 inside of three-dimensional working electrodes that may have narrow openings (e.g., honeycomb structures). The relative container diameters discussed herein can further configured to deposit varying amounts and geometries of conductive media via the second container 214.

A conductive media 206 can be disposed in the first cavity 202D such that the sensor system 200A includes the conductive media 206 as-assembled at the original equipment manufacturer (OEM). In other examples, the conductive media 206 can be supplied to a sensor system 200A such that it is deposited in the sensor system 200A outside of the OEM by a third party using the sensor system 200A. In this example, the sensor system 200A would not contain the conductive media, in contrast to what is depicted in FIG. 2A. The sensor body 210 can be a part of a kit that includes the conductive media 206 disposed in a vessel outside of the sensor body 210. The kit can include one or more sensor bodies 210 and one or more compositions of conductive media 206. Kitting can be used, for example, when the conductive media 206 may be UV-sensitive (and thus stored in a UV-resistant vessel), or to give the purchaser of the system options for sizes/shapes of sensor bodies 210 to use, or when two or more types of conductive media 206 may be used in combination in a sensor system. The conductive media 206 is discussed in detail below. The first container 202 is fluidly coupled to the second container 214 such that the conductive media 206 can be transported among and between the first container 202 and the second container 214. For example, the second cavity 214D can be configured to receive the conductive media 206 from the first cavity 202D in order to deposit the conductive media 206 on a working electrode (discussed below).

Further in the sensor system 200A, a first electrode 208 is positioned in the first cavity 202D. In one example, the first electrode 208 is in contact with and electrically coupled to the conductive media 206. As used herein, "electrically coupled" is used to refer to the coupling of two or more elements, such as a two or more sensor systems, or individual elements of a sensor system (e.g., two or more containers), or a coupling between a sensor system and a structure to be evaluated by the sensor system, which are configured form a circuit when in direct contact or when in contact with an electrically conductive media such as the conductive media 206.

The sensor system 200A further includes a first movable element 212 positioned in the first cavity 202D, and can be formed from a flexible material such as a polymer, an elastomer, or combinations thereof. The first movable element 212 can be moved from a first position to a second (or other subsequent) position within the first container 202 manually or using one or more electronic, magnetic, or combination actuators. The first movable element 212 is slidingly engaged with the first inside surface 202C of the first container 202 and is configured to cause the second container 214 to receive the conductive media 206 from the first container 202. The first movable element 212 can be moved manually or via one or more actuators operated automatically in response to execution of a program, or remotely. The second cavity 214D can be configured to receive the conductive media 206 from the first cavity 202D when pressure is applied to the first movable element 212. In the example shown in the sensor system 200A, the first electrode 208 is partially disposed in and either permanently or removably coupled to the first movable element 212 such that moving the first movable element 212 also moves the position of the first electrode 208. In examples where the second electrode 236 is used in the sensor system 200A, the second electrode 236 can be coupled to the first electrode 208 such that moving the first movable element 212 repositions the first electrode 208 and the second electrode 236. In other examples, the first electrode 208 and the second electrode 236 can each be positioned in separate, concentric containers such that one container having the first electrode 208 is positioned inside of a different container having the second electrode 236, or vice versa. In this example, the concentrically-configured containers are each filled with the same or different conductive media 206, and are electrically coupled to each other via the conductive media.

In one example, the first electrode 208 can be formed from a metallic material and can include a metallic salt formed thereon. In one example, the metallic salt can include the same metal or alloy of the metallic material. In other examples, the metallic salt can include a different metal or alloy than used to form the metallic material of the first electrode 208. In one examples, the first electrode 208 can be formed from silver and have a silver chloride coating formed thereon. The metallic salt coating can increase the conductivity and longevity of the first electrode 208. In other examples, the first electrode 208 can be formed from copper, graphite, titanium, brass, or platinum and may or may not have a metallic salt deposited thereon. Ferrocene-methanol (FcMeOH) can be used as a water-soluble ferrocene-based reference as the first electrode 208. In this example, which can be combined with other examples herein, the first electrode 208 can include a platinum electrode disposed in a container having ferrocene-methanol.

In one example, the first electrode 208 can be a linear element such that first electrode 208 is substantially straight and the ends of the first electrode 208 are not in contact with each other. In another example, the first electrode 208 can be configured as a closed loop. In another example, the first electrode 208 can be configured as a non-linear structure where the ends are not in contact with each other.

In some examples, which can be combined with other examples herein, the sensor system 200A further includes a second electrode 236. The second electrode 236 can be electrically coupled to the first electrode 208. Further, the second electrode 236 can be electrically coupled to the conductive media 206. In one example, the second electrode 236 can be formed from platinum. In other examples, the second electrode 236 can be formed from copper, graphite, titanium, or brass, and may or may not have a metallic salt deposited thereon. In another example, which can be combined with other examples herein, ferrocene-methanol (FcMeOH) can be used as a water-soluble ferrocene-based reference as the second electrode 236. In this example, the second electrode 236 can include a platinum electrode disposed in a container having ferrocene-methanol. In one example, the second electrode 236 can be a linear element such that first electrode 208 is substantially straight and the ends of the second electrode 236 are not in contact with each other. In another example, the second electrode 236 can be configured as a closed loop. In another example, the second electrode 236 can be configured as a non-linear structure where the ends are not in contact with each other. The type(s) of material from which the second electrode 236 is formed can be chosen based on factors including how many sensors are included in the sensor system, a geometry of the working electrode, such as working electrode 238 discussed below, a material of the working electrode, the type of test being performed, an amount of current applied to the electrochemical cell including the second electrode 236, the type of conductive media 206 used in the sensor system, a geometry of the second electrode 236, a material from which the first electrode 208 is formed, the configuration of the first electrode 208 relative to the second electrode 236, or other factors or combinations of factors.

Turning back to the conductive media 206, in one example, the conductive media 206 comprises a first element and a second element, wherein the first element is a conductive element that forms a colloidal suspension with the second element. The suspension of the first element in the second element forms the conductive media 206 used in the electrochemical cell. In some examples, which can be combined with other examples herein, the second element can be conducive on its own, e.g., prior to the first element being suspended therein. In one example, the first element is selected from the group consisting of: a salt, a plurality of polymer nanoparticles, a plurality of metallic nanoparticles, and combinations thereof. As used herein, a "nanoparticle" is a particle of any geometry (sphere, rod, polygon, or other geometries or combinations of geometries) having a maximum diameter of about 100 nanometers or less. The second element can be selected from the group consisting of: aloe, polyethylene glycol (PEG), polyacrylamide, silicones, polymer ionic liquids, polyelectrolytes (including polystyrene, sulfonates, and polyquats), and combinations thereof. In some examples, which can be combined with other examples herein, the second element includes two or more components and can include water.

In other examples, the conductive media 206 does not include water. The exclusion of water may increase the viscosity of the conductive media 206. Water-free conductive media can be used in instances where it may be desirable for the conductive media to hold its shape as-deposited. This may be the case where testing is to be performed over a matter of hours or days, as opposed to seconds or minutes, and/or when the conductive media 206 is deposited at an angle such that the conductive media 206 could slide or otherwise move or fall off of the surface upon which it is deposited. In one example, the water content of the conductive media 206 is from about 5 wt. % to about 65 wt. %. In another example, the water content of the conductive media 206 is from about 15 wt. % to about 45 wt. %. In another example, the water content of the conductive media 206 is from about 25 wt. % to about 35 wt. %. The water content of the conductive media 206 can be selected based upon factors including the geometry of the component being tested (e.g., the working electrode 238 discussed below) and the type or duration of the test being performed. In one example, the ratio of a volume percentage (vol. %) of the first element to the second element in the conductive media 206 is from about 1:100 to about 1:1. The ratio of a volume percentage (vol. %) of the first element to the second element in the conductive media 206 can be selected based upon factors including the geometry of the component being tested (e.g., the working electrode 238 discussed below) and the duration or type of test being performed. In another example, the ratio of a volume percentage (vol. %) of the first element to the second element in the conductive media 206 is from about 1:80 to about 1:20. In still another example, the ratio of a volume percentage (vol. %) of the first element to the second element in the conductive media 206 is from about 1:50 to about 1:10. Further, in one example, the conductive media 206 can be colorless and transparent. In some aspects of the sensor system 200A, or other sensor systems discussed herein, the conductive media 206 can be semi-transparent or opaque. In other configurations of the sensor system 200A or other sensor systems discussed herein, the conductive media 206 can be white.

In still other example sensor systems, the conductive media 206 can have a color such as red, green, blue, yellow, or combinations thereof. One or both of the color or the transparency/opaqueness of the conductive media 206 can be selected based upon factors including the test being performed, the appearance of the component being tested (e.g., the working electrode 238 discussed below), or to indicate a composition or material property of the conductive media 206. For example, the conductive media 206 can include a pH-sensitive dye that changes color when corrosion occurs during testing, thus producing a visual effect at the contact area that would complement the electrochemical information. In one example, which can be combined with other examples herein, a mixture of thymol blue, methyl red, bromothymol blue, thymol blue, and phenolphthalein may be added to the conductive media 206. A pH range could thus be indicated by a color when the pH is from less than about 3 (red) to greater than about 11 (violet). Intermediate colors include orange/yellow (indicating a pH from about 3 to about 6), green (indicating a pH of about pH 7 or neutral), and blue (indicating a pH of about 8 to about 11).

In one example, which can be combined with other examples herein, the conductive media 206 has a viscosity from about 50,000 centipoise (cps) to about 1 million cps. In another example, the conductive media 206 has a viscosity from about 125,000 centipoise (cps) to about 800,000 cps. In still another example, the conductive media 206 has a viscosity from about 250,000 centipoise (cps) to about 500,000 cps. The viscosity can be selected such that the conductive media 206 can be disposed in a controlled amount on a surface that is at any angle up to 180 degrees relative to a normal plane. That is, such that the conductive media 206 can be disposed and hold its shape and thus maintain its contact with the first electrode 208 (and the second electrode 236 when in use) as well as the first working electrode 238 to complete the electrochemical cell for a sufficient duration of time to complete the testing discussed herein.

In some configurations, the sensor system 200A further includes a power supply 218 configured to apply a current to the sensor system 200A. In one example, the power supply 218 can be configured to have a power capacity from about 1 microwatt (mW) to about 100 watts (W) and to apply a voltage from about 1 millivolt (mV) to about 100 volts (V) to one or more electrodes (208, 236) of the sensor system 200A. In another example, the power supply 218 can be configured to have a power capacity from about 1000 mW to about 80 W and to apply a voltage from about 100 mV to about 80V to one or more electrodes (208, 236) of the sensor system 200A. In yet another example, the power supply 218 can be configured to have a power capacity from about 1 W to about 60 W and to apply a voltage from about 1 to about 50V to one or more electrodes (e.g., 208, 236) of the sensor system 200A.

In some configurations, the sensor system 200A further includes hardware and software 216, including a non-transitory computer-readable medium, configured to execute one or more programs. Each program can be configured as a plurality of executable logic stored on a non-transitory computer-readable medium and communicatively coupled to the sensor system 200A such that a plurality of operations can be performed by the sensor system 200A when a program is executed. As used herein, "communicatively coupled" is to mean that two or more devices or aspects of devices are coupled via wired or wireless means such that information can be transmitted there between. In one example, a program can include disposing a first portion 206A of the conductive media 206 on a first working electrode 238.

The second electrode 236 can be configured, for example, as a loop, to extend into the second container 214 such that it can be extended into the first portion 206A of the conductive media 206 when the first portion 206A is disposed on the first working electrode 238. In this example, the second electrode 236 is electrically coupled to the first electrode 208 via the conductive media 206. In some examples, which can be combined with other examples herein, the second electrode 236 can be physically coupled to the first electrode 208. In other examples, the second electrode 236 is not physically coupled to the first electrode 208 when it is positioned in the first portion 206A of the conductive media 206. In still other examples, the second container 214 can have an internal metallic coating that acts as the second electrode 236.

The working electrodes discussed herein can include smooth surfaces, surfaces including three-dimensional nano-structures or three-dimensional macro-structures. As discussed herein, "nano-structures" are structures having up to a 100 nm maximum diameter. As discussed herein, "macro-structures" are structures visible to the naked eye without use of magnification, such as 110 discussed above in FIG. 1B (and discussed in detail below in FIG. 2B) including some honeycomb structures. The programs discussed herein can include a measurement program to determine a material property of a working electrode such as the first working electrode 238. The material property determined can include a composition, an electrical property, a chemical property, an electro-chemical property, or a physical property such as a material thickness or porosity (including pitting).

The electrochemical cell thus includes the first electrode 208, the second electrode 236, the first working electrode 238, and the conductive media 206, as well as the power supply 218. As discussed in the method 600 below, a circuit is formed between the power supply 218, one or both of the first electrode 208 and the second electrode 236, and the conductive media 206 and executing one or more electrochemical tests. Data obtained in response to the execution of the one or more electrochemical tests can be analyzed by the sensor system 200A. In another example, data obtained in response to the execution of the one or more electrochemical tests can be transmitted from and by the sensor system 200A to a remote server via one or more wireless or wired communication networks.

Figure 2B:
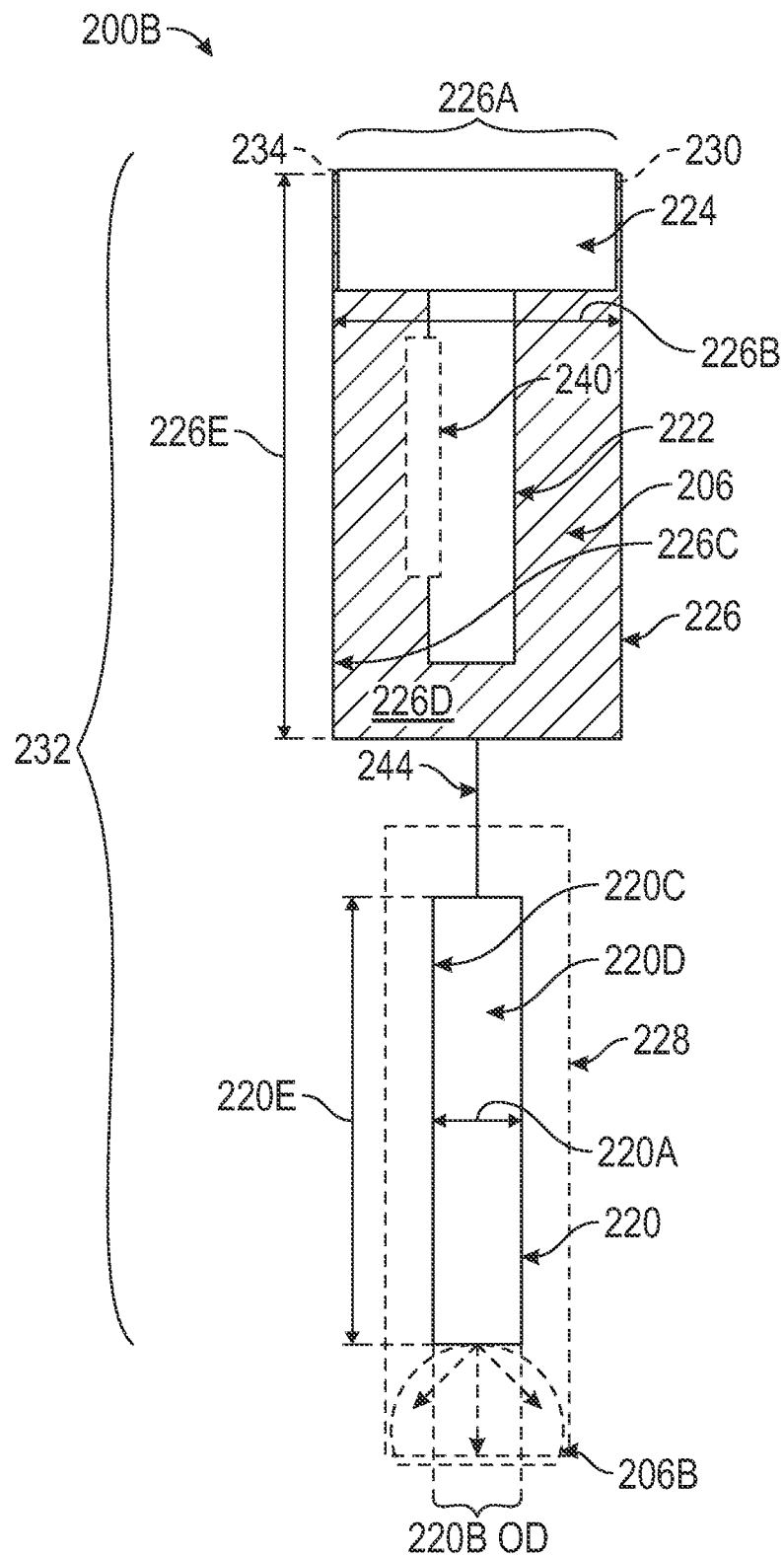
FIG. 2B depicts another example sensor system according to aspects of the present disclosure.

FIG. 2B depicts another example sensor system 200B according to aspects of the present disclosure. The sensor system 200B includes a sensor body 232, the sensor body 232 includes a first container 226 that can be removably or permanently coupled to a second container 220. In one example, the first container 226 is fluidly coupled to the second container 220 via a connection mechanism 244. The connection mechanism 244 can include a leur lock. In one example, the first container 226 has a first inside diameter 226B, a first outside diameter 226A, a first inside surface 226C defining a first cavity 226D. The first container 226 can further be defined by a first length 226E. In another example, which can be combined with other examples herein, the second container 220 has a second inside diameter 220A, an outside diameter 220B, and a second inside surface 220C defining a second cavity 220D. The second container 220 can further have a second length 220E. In some examples, the first inside diameter 220B of the first container 226 is greater than the second inside diameter 220A of the second container 220. In one example, the first length 226E of the first container 226 can be greater than the second length 220E of the second container 220 by from about 0% (e.g., substantially the same length) to about 100%. In another example, the first length 226E of the first container 226 can be greater than the second length 220E of the second container 220 by from about 30% to about 75%. The relative container lengths discussed herein can configured as such for varying purposes, including when the working electrodes discussed herein have various geometries and configurations. For example, some relative container lengths can be desirable when depositing conductive media 206 on one or more surfaces of a working electrode. The relative container lengths discussed herein can further configured to retain varying amounts of conductive media in the first container 226. In yet another example, the first length 226E of the first container 226 can be greater than the second length 220E of the second container 220 by from about 45% to about 60%.

In some examples, the first inside diameter 226B of the first container 226 is greater than the second inside diameter 220A of the second container 220. In one example, the first inside diameter 226B of the first container 226 is greater than the second inside diameter 220A of the second container 220 by from about 10% to about 100%. In another example, the first inside diameter 226B of the first container 226 is greater than the second inside diameter 220A of the second container 220 by from about 20% to about 70%. In still another example, the first inside diameter 226B of the first container 226 is greater than the second inside diameter 220A of the second container 220 by from about 35% to about 50%. The relative container diameters discussed herein can configured as such for varying purposes, including when the working electrodes discussed herein have various geometries and configurations. For example, some relative container lengths can be desirable when depositing conductive media 206 inside of three-dimensional working electrodes that may have narrow openings (e.g., honeycomb structures). The relative container diameters discussed herein can further configured to deposit varying amounts and geometries of conductive media via the second container 220.

A conductive media 206 can be disposed in the first cavity 226D. In other examples of the sensor system 200B, similarly to what is discussed above with respect to the sensor system 200A, the sensor system 200B may not contain the conductive media 206 as-fabricated. The first container 226 being fluidly coupled to the second container 220 such that the conductive media 206 can be transported among and between the first container 226 and the second container 220. For example, the second cavity 220D can be configured to receive the conductive media 206 from the first cavity 226D. Further in the sensor system 200B, a first electrode 222 is positioned in the first cavity 226D. In one example, the first electrode 222 is electrically coupled to the conductive media 206. The electric coupling of the first electrode 222 to the conductive media 206 forms the electrochemical cell discussed herein.

The sensor system 200B further includes a second movable element 224 positioned in the first cavity 226D. The first movable element 212 can be moved manually or via one or more actuators operated automatically in response to execution of a program, or remotely, can be moved manually or via one or more actuators operated automatically in response to execution of a program, or remotely. The second movable element 224 can be moved from a first position to a second (or other subsequent) position within the first container 226 manually or using one or more electronic, magnetic, or combination actuators. The second movable element 224 is slidingly engaged with the first inside surface 226C of the first container 226. The second movable element 224 is configured to cause the second container 220 to receive the conductive media 206 from the first container 226 (e.g., the second cavity 220D can be configured to receive the conductive media 206 from the first cavity 226D when pressure is applied to the second movable element 224). In the example shown in the sensor system 200B, in contrast to the sensor system 200A of FIG. 2A, the first electrode 222 is permanently or removably coupled to, instead of being disposed in, the second movable element 224 such that moving the second movable element 224 also moves the position of the first electrode 222. The first electrode 222 can be coupled to the second movable element 224 in this manner depending upon factors such as the geometry of one or both of the first electrode 222 or the second movable element 224. For example, the second movable element 224 may have a thickness and a rigidity such that forming an aperture therein would compromise the integrity of the second movable element. In another example, the second movable element 224 may have an adhesive disposed thereon to which the first electrode 222 can be removably or permanently coupled for rapid and/or automated assembly purposes. In examples where the second electrode 240 is used in the sensor system 200B, the second electrode 240 can be coupled to the first electrode 222 such that moving the second movable element 224 repositions the first electrode 222 and the second electrode 240. This may be the configuration of the first electrode 222 and the second electrode 240 to maintain an alignment between the first electrode 222 and the second electrode 240 with respect to the sensor body 210.

In one example, the first electrode 222 can be formed from a metallic material and can include a metallic salt formed thereon. In one example, the metallic salt can include the same metal or alloy of the metallic material. In other examples, the metallic salt can include a different metal or alloy than used to form the metallic material of the first electrode 222. In one examples, the first electrode 222 can be formed from silver and have a silver chloride coating formed thereon. The first electrode 222 can be formed from other materials similar to the materials discussed with respect to the first electrode 208 in FIG. 2A, including copper, graphite, titanium, brass, platinum, or ferrocenemethanol (FcMeOH) in combination with platinum. In one example, the first electrode 222 can be a linear element such that the ends of the first electrode 222 are not in contact with each other. In another example, the first electrode 222 can be configured as a closed loop.

In some examples, which can be combined with other examples herein, the sensor system 200B further includes a second electrode 240. The second electrode 240 can be electrically coupled to the first electrode 222. Further, the second electrode 240 can be electrically coupled to the conductive media 206. In some examples, the second electrode 240 can be formed from platinum. The second electrode 240 can also be formed from materials similar to the materials discussed with respect to the second electrode 236 in FIG. 2A, including copper, graphite, titanium, brass, silver, or ferrocenemethanol (FcMeOH) in combination with platinum. In one example, the second electrode 240 can be a linear element such that the ends of the second electrode 240 are not in contact with each other. In another example, the second electrode 240 can be configured as a closed loop.

The sensor system 200B further includes a power supply 234 configured to apply a current to the sensor system 200B. The power supply 234 can be configured similarly to the power supply 218 in FIG. 2A. In some examples, the sensor system 200B further includes hardware and software 230, including a non-transitory computer-readable medium, configured to execute one or more programs. Each program can be configured as a plurality of executable logic stored on a non-transitory computer-readable medium and communicatively coupled to the sensor system 200B such that a plurality of operations can be performed by the sensor system 200B when a program is executed. In one example, a program can include disposing a second portion 206B of the conductive media 206 on a second working electrode 228. The program can further include forming a circuit between the power supply 234, one or both of the first electrode 222 and the second electrode 240, and the conductive media 206 and executing one or more electrochemical tests. Data obtained in response to the execution of the one or more electrochemical tests can be analyzed by the sensor system 200B. In another example, data obtained in response to the execution of the one or more electrochemical tests can be transmitted from and by the sensor system 200B to a remote server via one or more wireless or wired communication networks.

The working electrode 228 in FIG. 2B is a three-dimensional structure, such as the three-dimensional structure 110 shown and discussed in FIG. 1B above. Accordingly, the second portion 206B of the conductive media 206 can be in contact with multiple surfaces of the three-dimensional structure of the second working electrode 228, in contrast to the first portion 206A of the conductive media disposed on the first working electrode 238 in FIG. 2A which can be in contact with a single surface. In the example in FIG. 2B, the second container 220 can be positioned inside of the second working electrode 228 to deposit the second portion 206B of the conductive media 206. In some examples, the first working electrode 238 includes a surface structure such as a porosity or a plurality of nano-structures such that the first portion 206A of the conductive media 206 is in contact with two or more surfaces of the first working electrode because of the structure of the surface. A "nano-structure" includes one or more features having a maximum height of 100 nm or less. In some examples, the first working electrode 238, or other working electrodes discussed herein, can include a microstructure. As discussed herein, a "microstructure" includes one or more features having a maximum dimension from about 101 nanometers (nm) to about 0.1 millimeters (mm).

While the sensor systems (200A, 200B) in FIGS. 2A and 2B each show a sensor system including a single sensor, in other examples, sensor systems can include two or more sensors which can be arranged in an array, as discussed below.

Figure 3A:
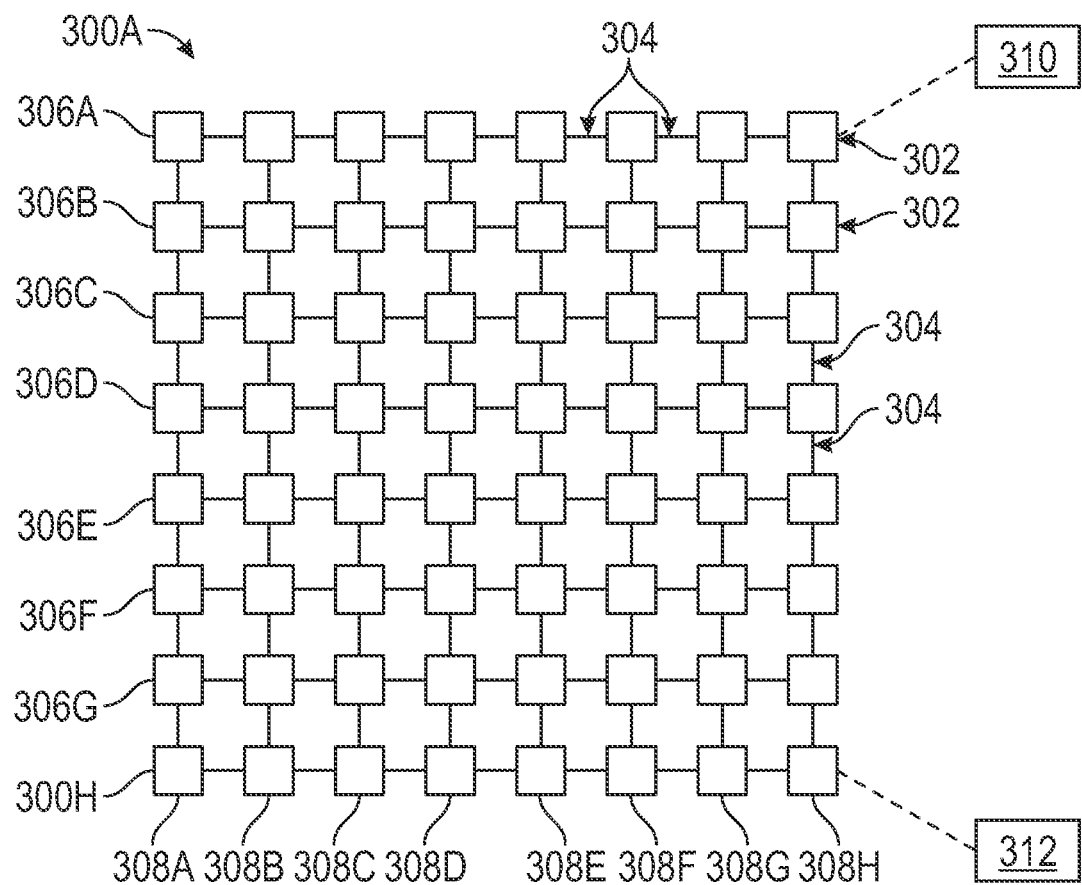
FIG. 3A depicts a sensor system configured as an array of sensors according to aspects of the present disclosure.

FIG. 3A depicts a sensor system 300A configured as an array of sensors according to aspects of the present disclosure. The sensor system 300A includes a plurality of sensors 302. In various examples, each sensor 302 of the plurality of sensors 302 can be configured as the sensors shown in either of FIG. 2A or 2B. In the sensor system 300A, each sensor 302 of the plurality of sensors 302 is connected to at least one adjacent sensor 302 via a connection mechanism 304 along a shared plane. This enables a plurality of portions of conductive media to be positioned on a working electrode such that one or more material properties can be measured across a working electrode in a shorter period of time than it would take to use a single sensor to obtain data in a plurality of locations. Thus, the plurality of sensors are arranged in a plurality of rows (306A-306H), and a plurality of columns (308A-308H). In one example, each row of the plurality of rows (306A-306H) is positioned at substantially a right angle along the shared plane as compared to each column of the plurality of columns (308A-308H). While an equal number of rows and columns are shown in FIG. 3A, in another example, the sensor system 300A can include more rows than columns. In other examples, the sensor system 300A can include more columns than rows. In one example, the connection mechanisms 304 are formed from a metallic material. In another example, the connection mechanisms 304 are formed from a polymer or elastomer. In other examples, the connection mechanisms 304 are formed from a combination of two or more metallic, polymer, elastomer, or ceramic materials. In yet another example, the connection mechanisms 304 are formed from a conductive material. In one example, the connection mechanisms 304 are formed from a rigid material, such that the plurality of sensors 302 are fixed along the shared plane. In another example, the connection mechanisms 304 are formed from a semi-rigid or flexible material such that the plurality of sensors 302 can conform to surfaces of various angles and curvatures, such as the outside surface 102 or the inside surface 104 of the component 100A in FIG. 1A, in order to deposit conductive media in multiple positions.

Further the sensor system 300A further includes a power supply 312 configured to apply a current to the sensor system 300A. The power supply 312 can be configured similarly to the power supply 218 in FIG. 2A. In some examples, the sensor system 300A further includes hardware and software 310, including a non-transitory computer-readable medium, configured to execute one or more programs. Each program can be configured as a plurality of executable logic communicatively coupled to the sensor system 300A such that a plurality of operations can be performed by the sensor system 300A when a program is executed.

Figure 3B:
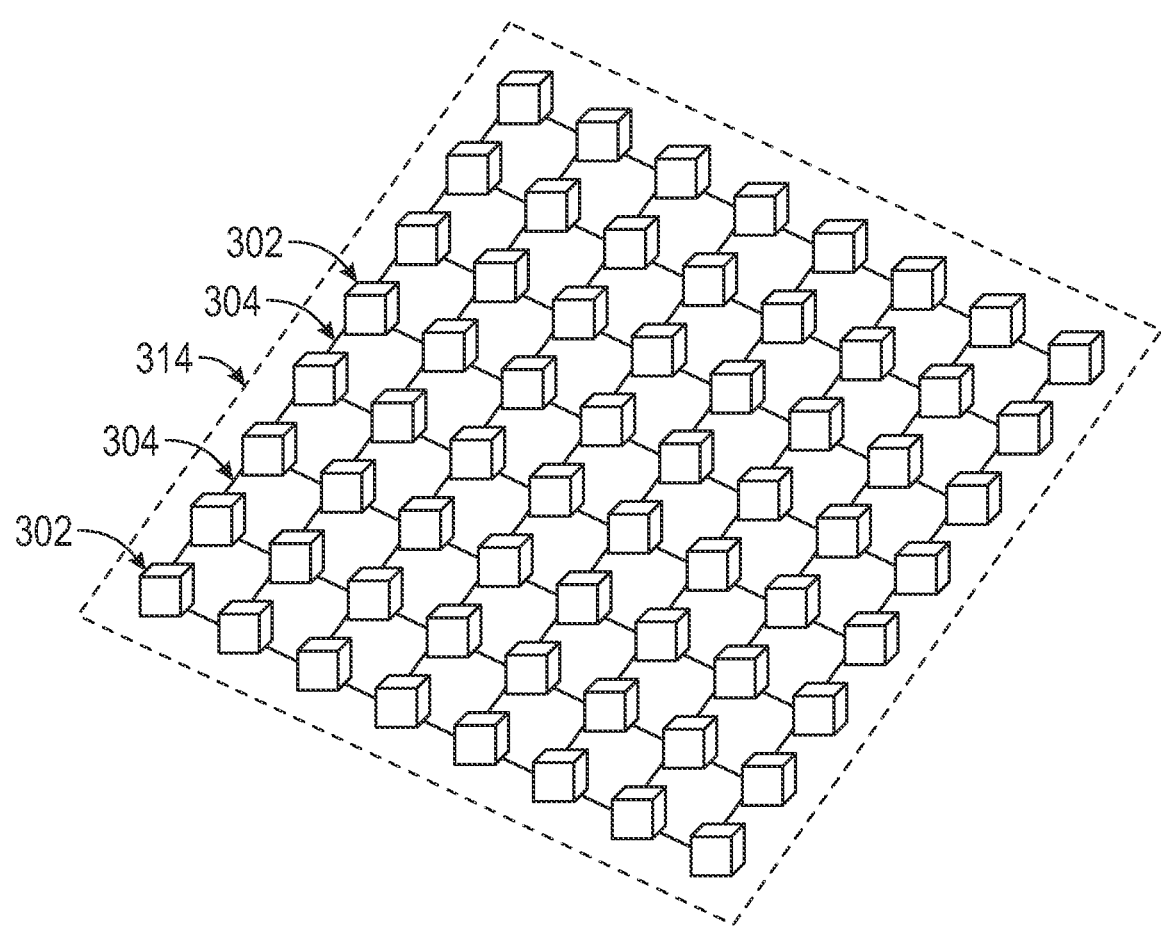
FIG. 3B is a perspective view of the sensor system 300A in FIG. 3A.

FIG. 3B is a perspective view of the sensor system 300A in FIG. 3A. FIG. 300B shows the plurality of sensors 302 and the connection mechanisms 304 disposed there between. FIG. 300B also illustrates the plane 314 along which the plurality of sensors 302 can be positioned and aligned.

Figure 4:
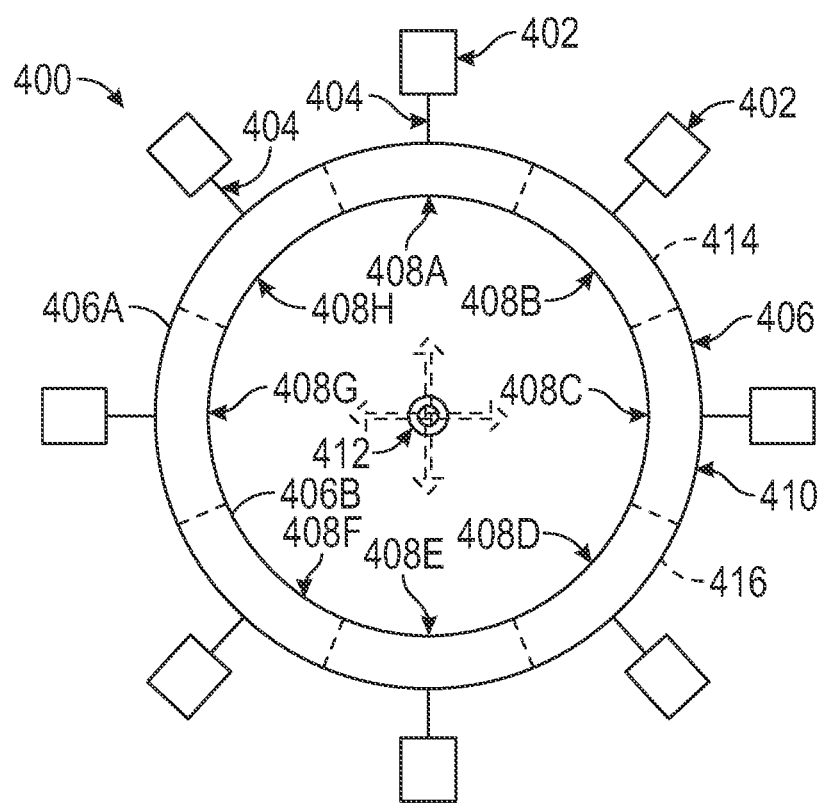
FIG. 4 depicts a sensor system configured as an array of sensors according to aspects of the present disclosure.

FIG. 4 depicts a sensor system 400 configured as an array of sensors according to aspects of the present disclosure. The sensor system 400 includes a plurality of sensors 402 that can be configured similarly to either of the sensors shown in the sensor systems in FIG. 2A or 2B. Each sensor 402 of the plurality of sensors 402 is coupled to a sensor support 406 having an outside surface 406A, an inside surface 406B, and a central axis 412. The sensor support 406 acts as a mechanism by which the plurality of sensors 402 can be positioned in a plurality of locations across a working electrode in order to obtain material property data across the working electrode in less time than it would take to obtain the same data using a single sensor. In some examples, the sensor system 400 further includes hardware and software 414, including a non-transitory computer-readable medium, configured to execute one or more programs. Each program can be configured as a plurality of executable logic stored on a non-transitory computer-readable medium and communicatively coupled to the sensor system 400 such that a plurality of operations can be performed by the sensor system 400 when a program is executed. In one example, the sensor support 406 is configured as a circular ring. In another example, the sensor support 406 can be configured as an elliptical ring. In one example, each sensor 402 of the plurality of sensors 402 is removably coupled to the sensor support 406 via at least one connection mechanism 404 of the plurality of connection mechanisms 404. The sensor support 406 includes a plurality of portions (408A-408H), the dotted lines 410 indicate the separation between each portion of the plurality of portions (408A-408H). While each portion (408A-408H) is shown in FIG. 4 to include a single sensor of the plurality of sensors 402, in other examples, each portion (408A-408H) includes two or more sensors of the plurality of sensors 402. Each portion of the plurality of portions (408A-408H) is removably coupled to an adjacent portion (408A-408H), wherein each portion (408A-408H) is independently adjustable relative to the central axis 412 (as indicated by the dotted arrows). Because each portion is adjustable, the sensor system 400 can be used to measure material properties across working electrodes of varying sizes and geometries. The sensor system 400 could be used to measure a portion of or the entirety of the inside surface 104 of a component 100A shown in FIG. 1A. In this example, a plurality of portions of conductive media (e.g., 206 from FIGS. 2A and 2B above) can be simultaneously or sequentially deposited on the inside surface 104 and the conductive media is formed as to be robust enough as to be deposited up to 180 degrees (e.g., upside down) from a normal plane.

Figure 5:
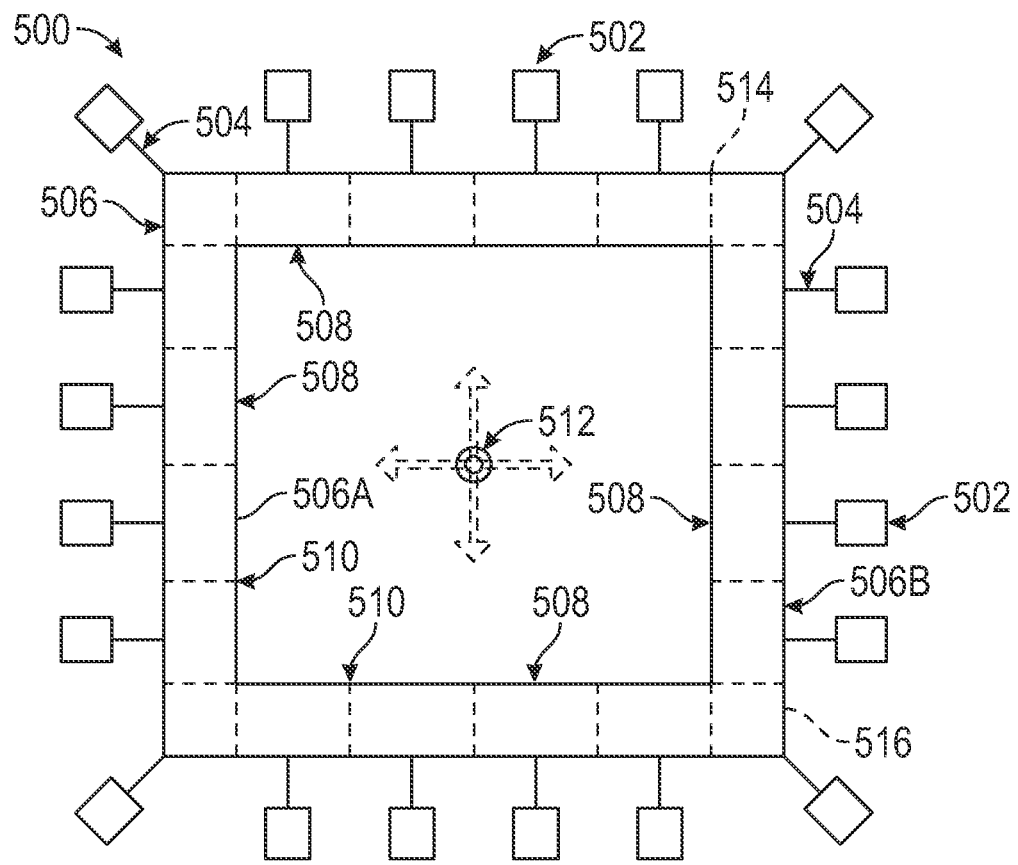
FIG. 5 depicts a sensor system configured as an array of sensors according to aspects of the present disclosure.

FIG. 5 depicts a sensor system 500 configured as an array of sensors according to aspects of the present disclosure. The sensor system 500 includes a plurality of sensors 502 that can be configured similarly to either of the sensors shown in the sensor systems in FIG. 2A or 2B. Each sensor 502 of the plurality of sensors 502 is coupled to a sensor support 506 having an outside surface 506A, an inside surface 506B, and a central axis 512. In some examples, the sensor system 500 further includes hardware and software 514, including a non-transitory computer-readable medium, configured to execute one or more programs. Each program can be configured as a plurality of executable logic stored on a non-transitory computer-readable medium and communicatively coupled to the sensor system 500 such that a plurality of operations can be performed by the sensor system 500 when a program is executed. The sensor support 506 is shown as a four-sided polygon in FIG. 5. It is contemplated that the sensor support 506 can be configured as a triangle, or as a polygon having five or more sides. In one example, each sensor 502 of the plurality of sensors 502 is removably coupled to the sensor support 506 via at least one connection mechanism 504 of the plurality of connection mechanisms 504. The sensor support 406 includes a plurality of portions 508, the dotted lines 510 indicate the separation between each portion of the plurality of portions 508. While each portion 508 is shown in FIG. 5 to include a single sensor of the plurality of sensors 502, in other examples, each portion 508 includes two or more sensors of the plurality of sensors 502. Each portion of the plurality of portions 508 is removably coupled to an adjacent portion 508, wherein each portion 508 is independently adjustable relative to the central axis 512 (as indicated by the dotted arrows). The sensor system 500 could be used to measure a portion of or the entirety a plurality of surfaces that may or may not be interconnected. In this example, a plurality of portions of conductive media (e.g., 206 from FIGS. 2A and 2B above) can be simultaneously or sequentially deposited on the plurality of surfaces and the conductive media is formed as to be robust enough as to be deposited up to 180 degrees (e.g., upside down) from a normal plane.

Figure 6:
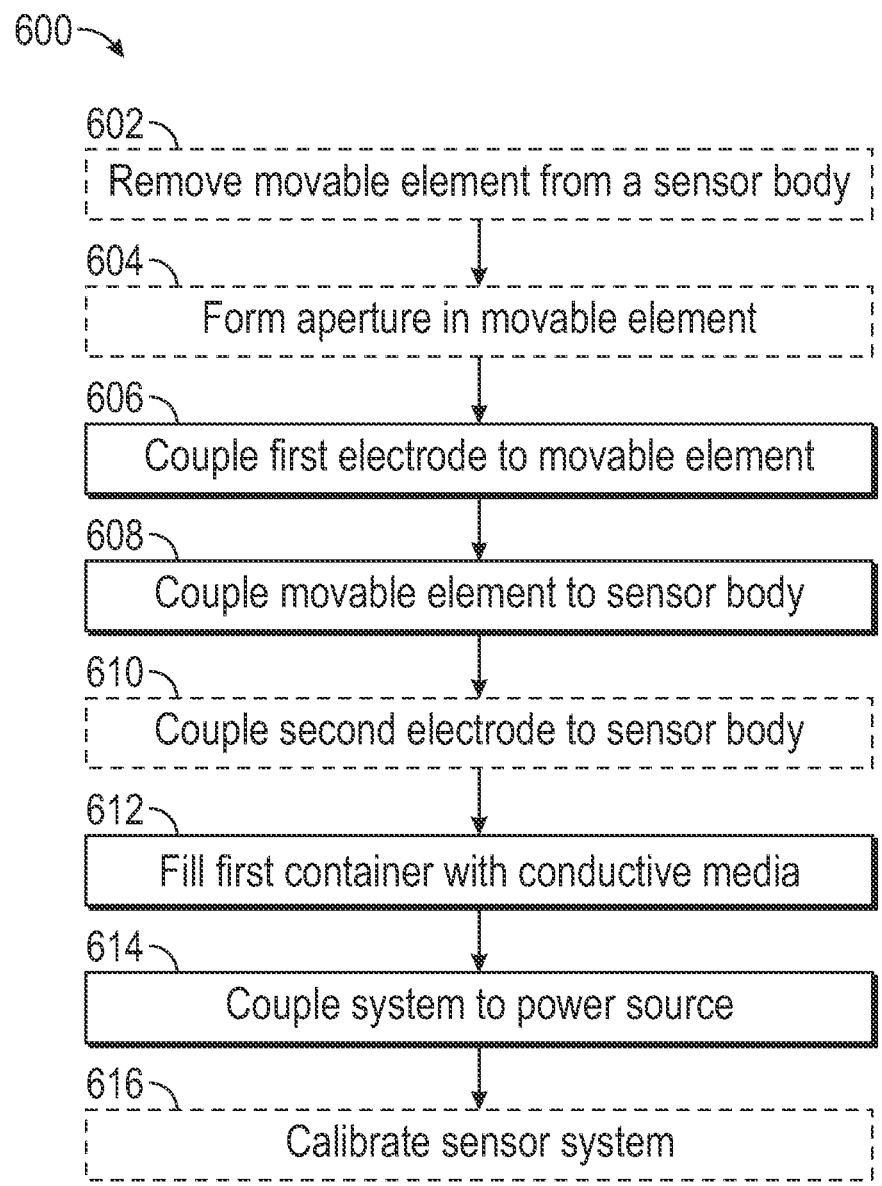
FIG. 6 is a flow chart of a method of fabricating sensor systems according to aspects of the present disclosure.

FIG. 6 is a flow chart of a method 600 of fabricating the sensor systems according to aspects of the present disclosure. The method 600 includes the optional operations 602, 604, and 606 of assembling a sensor system. In one example, at operation 602 (602—Remove movable element from a sensor body), a movable element is removed from a sensor body. At operation 604 (604—Form aperture in movable element), an aperture is formed through the movable element such that a first electrode can be coupled thereto at operation 606 (606—Couple first electrode to movable element). In one example, at operation 606, the first electrode is inserted into the aperture of the movable element. In another example, where operation 604 is not executed, the first electrode is coupled to the movable element at operation 606 via adhesive or other means without formation of an aperture. At operation 608 (608—Couple movable element to sensor body), the movable element having the first electrode coupled thereto is coupled to the sensor body. In some examples, the sensor system includes one electrode in the sensor body and electrically couples to a working electrode via the conductive media (such as the conductive media 206 discussed above). In other examples, a second electrode is coupled to the sensor system, e.g., to the first electrode, at operation 610 (610—Couple second electrode to sensor body) to form an electrode assembly. At operation 612 (612—Fill first container with conductive media), the first container of the sensor body is filled with conductive media. In some examples, operation 612 occurs after operation 608. In other examples, operation 614 occurs after operation 610. In still other examples, operation 614 occurs prior to operation 610 such that the electrode assembly of the at least one electrode and movable element is disposed into the conductive media.

Figure 7:
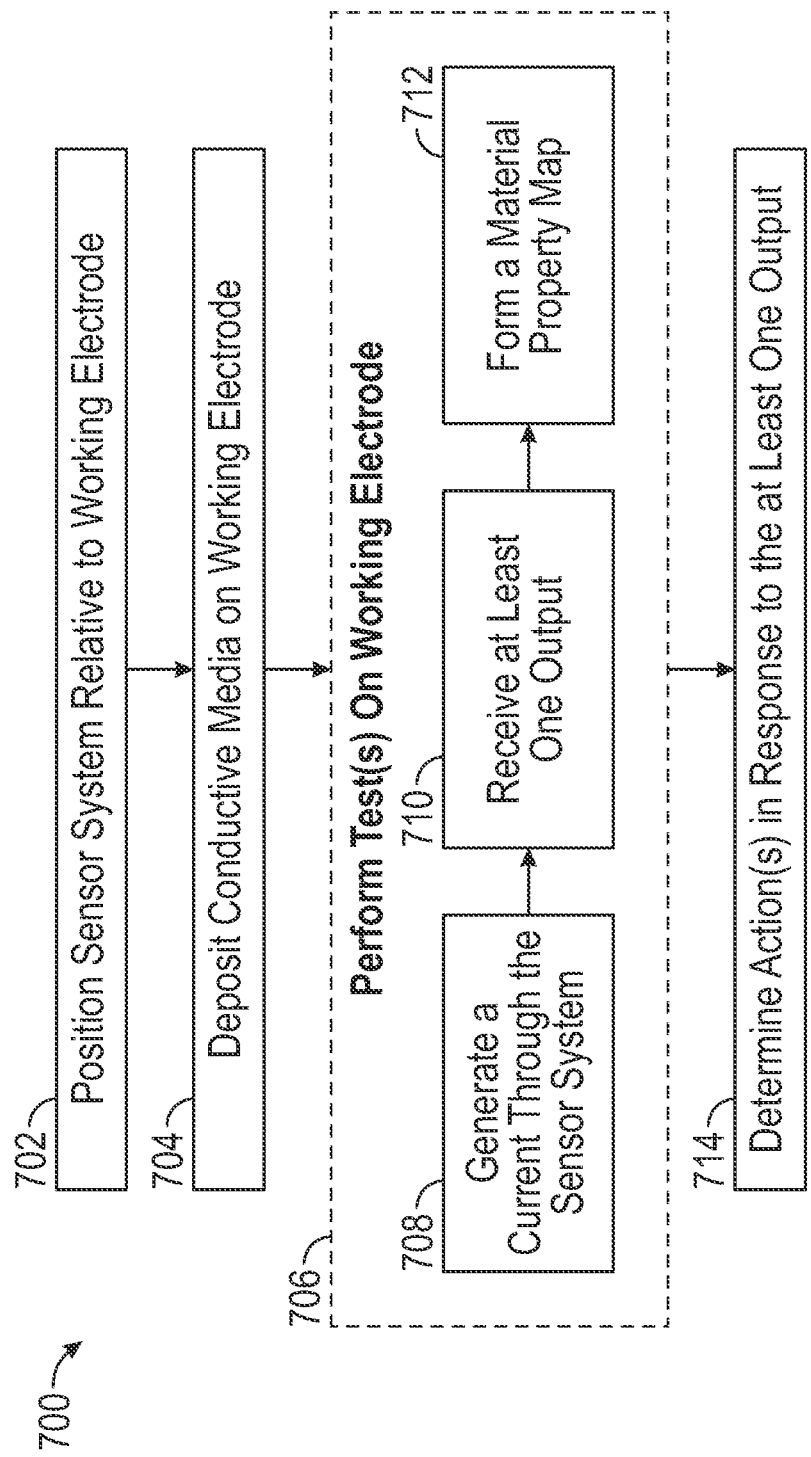
FIG. 7 is a flow chart of a method of testing using the sensor systems according to aspects of the present disclosure.

In some examples of the method 600, at operation 616 (616—Calibrate sensor system) the sensor system can be calibrated. Calibration can occur via various means including using a working electrode having a known electric potential or other property to determine the accuracy of the sensor system, including the integrity of its components. In some examples, the calibration at operation 616 may include sensor system maintenance, including replacement of one or more electrodes or replenishment/replacement of the conductive media. FIG. 7 is a flow chart of a method of testing using the sensor systems according to aspects of the present disclosure. At operation 702 (702—Position sensor system relative to working electrode), the sensor system is positioned in relation to a working electrode. As discussed above, the sensor system includes one or more sensors. The working electrode can include one or more surfaces of varying materials and surface roughness/structures. At operation 704 (704—Deposit conductive media on working electrode), a conductive media is deposited on, or inside of in the example of a honeycomb structure, a working electrode. The conductive media is electrically coupled to at least one electrode of the sensor system, wherein depositing the conductive media on the working electrode electrically couples the working electrode to the sensor system.

At operation 706 (706—Perform test(s) on working electrode), one or more electrochemical tests can be performed to determine one or more material properties of the working electrode. The electrochemical tests can include cyclic voltammetry, potentiodynamic scanning, chronoamperometry, pulse voltammetry, corrosion detection, or electrochemical polymerization. The electrochemical tests can be used to determine aspects of a working electrode based on the difference in potential across the working electrode interface, a reaction rate based on a current density, or a surface impedance. In one example, operation 706 includes operation 708 (708—Generate a current through the sensor system) generating, via the power supply, a current through the sensor system and the working electrode (e.g., the electrochemical cell) for a predetermined period of time. The predetermined period of time can be from about 0.1 second to about 10 hours. In another example, the predetermined period of time can be from about 10 seconds to about 2 hours. In still another example, the predetermined period of time can be from about 30 minutes to about 90 minutes. The predetermined period of time can be based on factors including the type of working electrode being tested, the test(s) being performed, the number of sensors of the sensor system being used to perform the test(s), or other factors.

In one example, the power supply is pulsed, creating a pulsed current through the electrochemical cell. The predetermined period of time for each pulse can be from about 0.1 second to about 10 hours. In another example, the predetermined period of time can be from about 10 seconds to about 2 hours. In still another example, the predetermined period of time can be from about 30 minutes to about 90 minutes. The predetermined period of time can be based on factors including the type of working electrode being tested, the test(s) being performed, the number of sensors of the sensor system being used to perform the test(s), or other factors. In some examples, which can be combined with other examples herein, operation 706 further includes operation 710 (710—Receive at least one output) receiving, in response to the generating of the current, at least one output, wherein the at least one output indicates an electrochemical (material) property of the working electrode. In some examples, two or more of operations 702, 704, or 706 can be repeated in an iterative fashion by a single sensor or using a sensor array in order to obtain data across a plurality of locations of a working electrode. Subsequently, at operation 714 (714—Determine action(s) in response to the at least one output) one or more actions can be determined based on the output received at operation 710. The one or more actions determined at operation 714 can include (1) leaving the component in use and continuing to follow an existing maintenance schedule, (2) removing the component from use and scheduling maintenance for a future time period, (3) performing maintenance at the site of testing, or (4) transporting the component to a separate location for maintenance.

In some examples, when a sensor system having an array is used, or when a sensor system having a single sensor is employed a plurality of times across a working electrode, the operation 706 further includes operation 712 (712—Form a material property map) forming a material property map of a portion of the working electrode. In an example where a map is formed at operation 712 using a sensor system having an array, prior to applying the current, at operation 702, the plurality of sensors are positioned in a plurality of locations along at least one surface of the working electrode the conductive media is deposited on the working electrode in the plurality of locations to electrically couple each sensor of the plurality of sensors to the working electrode. As discussed above, in some examples the working electrode comprises a three-dimensional component such as a honeycomb structure including a plurality of surfaces such that at least one sensor of the sensor system is positioned inside of the working electrode, and wherein the depositing of the conductive media at operation 618 causes the conductive media to contact two or more surfaces of the plurality of surfaces.

Accordingly, using the sensor systems and methods of used discussed herein, non-destructive testing is used to rapidly obtain material properties and characterize materials. The methods discussed herein can be performed in a matter of minutes, for example, from about 1 minute to about 60 minutes depending upon what percentage of the working electrode is tested. Thus, the integrity of the components being tested can be quickly determined, and repairs or other maintenance can be scheduled according to the test results. Further, foreign materials formed or deposited on the component can be characterized to determine if those materials are harmful, in which case repairs may be executed, or innocuous.

In the current disclosure, reference is made to various aspects. However, it should be understood that the present disclosure is not limited to specific described aspects. Instead, any combination of the above features and elements, whether related to different aspects or not, is contemplated to implement and practice the teachings provided herein. Additionally, when elements of the aspects are described in the form of "at least one of A and B," it will be understood that aspects including element A exclusively, including element B exclusively, and including element A and B are each contemplated. Furthermore, although some aspects may achieve advantages over other possible solutions and/or over the prior art, whether or not a particular advantage is achieved by a given aspect is not limiting of the present disclosure. Thus, the aspects, features, aspects and advantages disclosed herein are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

As will be appreciated by one skilled in the art, aspects described herein may be embodied as a system, method or computer program product. Accordingly, aspects may take the form of an entirely hardware aspect, an entirely software aspect (including firmware, resident software, micro-code, etc.) or an aspect combining software and hardware aspects that may all generally be referred to herein as a "circuit," "module" or "system." Furthermore, aspects described herein may take the form of a computer program product embodied in one or more computer readable storage medium(s) having computer readable program code embodied thereon.

Program code embodied on a computer readable storage medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described herein with reference to flowchart illustrations and/or block diagrams of methods, apparatuses (systems), and computer program products according to aspects of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block(s) of the flowchart illustrations and/or block diagrams.

These computer program instructions may also be stored in a computer readable medium that can direct a computer, other programmable data processing apparatus, or other device to function in a particular manner, such that the instructions stored in the computer readable medium produce an article of manufacture including instructions which implement the function/act specified in the block(s) of the flowchart illustrations and/or block diagrams.

The computer program instructions may also be loaded onto a computer, other programmable data processing apparatus, or other device to cause a series of operational steps to be performed on the computer, other programmable apparatus or other device to produce a computer implemented process such that the instructions which execute on the computer, other programmable data processing apparatus, or other device provide processes for implementing the functions/acts specified in the block(s) of the flowchart illustrations and/or block diagrams.

The flowchart illustrations and block diagrams in the Figures illustrate the architecture, functionality, and operation of possible implementations of systems, methods, and computer program products according to various aspects of the present disclosure. In this regard, each block in the flowchart illustrations or block diagrams may represent a module, segment, or portion of code, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order or out of order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

While the foregoing is directed to aspects of the present disclosure, other and further aspects of the disclosure may be devised without departing from the basic scope thereof, and the scope thereof is determined by the claims that follow.

What is claimed is:

1. A sensor system, comprising:
a sensor, comprising:
a sensor body having a first container and a second container, the first container having a first inside surface defining a first cavity, the second container having a second inside surface defining a second cavity, and the first container being fluidly coupled to the second container;
a first electrode positioned in the first cavity, the first electrode being electrically coupled to a conductive media having a water content of about 20 wt. % to about 45 wt. %, wherein the conductive media comprises:
a first element comprising a conductive element comprising a plurality of metallic nanoparticles or a plurality of polymer nanoparticles; and
a second element, wherein the first element is present as a colloidal suspension with the second element; and
a first movable element positioned in the first cavity, the first movable element being slidingly engaged with the first inside surface of the first container and configured to cause the second container to receive the conductive media from the first container.

2. The sensor system of claim 1, further comprising the first electrode being formed from silver and having a silver chloride coating formed thereon.

3. The sensor system of claim 1, further comprising:
the conductive media disposed in the first cavity; and a second electrode, the second electrode being electrically coupled to the first electrode and electrically coupled to the conductive media, the second electrode being formed from platinum, the second cavity being configured to receive the conductive media from the first cavity.

4. The sensor system of claim 3, wherein the second electrode is configured as a linear element or as a closed loop.

5. The sensor system of claim 1, wherein a first inside diameter of the first container is greater than a second inside diameter of the second container.

6. The sensor system of claim 1, further comprising a plurality of sensors, each sensor of the plurality of sensors being connected to at least one adjacent sensor via a connection mechanism along a shared plane.

7. The sensor system of claim 1, further comprising:
a plurality of sensors;
a plurality of connection mechanisms; and
a sensor support having an outside surface, an inside surface, and a central axis, wherein each sensor of the plurality of sensors is removably coupled to the sensor support via at least one connection mechanism of the plurality of connection mechanisms.

8. The sensor system of claim 7, wherein the sensor support includes a plurality of portions, each portion of the plurality of portions being removably coupled to an adjacent portion, wherein each portion is independently adjustable relative to the central axis.

9. A sensor system, comprising:
a sensor, comprising:
- a sensor body having a first container and a second container, the first container having a first inside surface, the first inside surface defining a first cavity, the second container having a second inside surface defining a second cavity, the second container being fluidly coupled to the first container;
- a conductive media disposed in the first cavity, the second cavity being configured to receive the conductive media from the first cavity, wherein the conductive media has a water content of about 20 wt. % to about 45 wt. %, wherein the conductive media comprises:
  - a first element comprising a conductive element comprising a plurality of metallic nanoparticles or a plurality of polymer nanoparticles; and
  - a second element, wherein the first element is present as a colloidal suspension with the second element;
- a first electrode disposed in the first cavity and electrically coupled to the conductive media, the first electrode comprising a metallic wire having a metallic salt coating;
- a second electrode, the second electrode being electrically coupled to the first electrode and to the conductive media; and
- a first movable element positioned in the first cavity, the first movable element being slidingly engaged with the first inside surface of the first container and configured to cause the second container to receive the conductive media from the first container.

10. The sensor system of claim 9, further comprising a power supply configured to apply a current to the sensor system.

11. The sensor system of claim 9, wherein the conductive media has a viscosity from about 50,000 centipoise (cps) to about 1 million cps.

12. The sensor system of claim 9, wherein the second element is selected from the group consisting of: aloe, polyethylene glycol (PEG), polyacrylamide, and combinations thereof.

13. The sensor system of claim 9, wherein a ratio of a volume percentage (vol. %) of the first element to the second element in the conductive media is from about 1:100 to about 1:1.

14. The sensor system of claim 9, further comprising a plurality of executable logic stored on a non-transitory computer-readable medium communicatively coupled to the sensor system, the plurality of executable logic being configured to execute a measurement program to determine a material property of a working electrode, the working electrode having a portion of the conductive media disposed thereon and being electrically coupled to the sensor body via the portion of the conductive media.

15. The sensor system of claim 9, wherein the conductive media has a water content from about 25 wt. % to about 35 wt. %.

16. The sensor system of claim 9, wherein the plurality of polymer nanoparticles or the plurality of metallic nanoparticles each, independently, has a diameter of about 1 nm to about 100 nm.

* * * * *